US006452180B1

(12) United States Patent
Nistler et al.

(10) Patent No.: US 6,452,180 B1
(45) Date of Patent: Sep. 17, 2002

(54) INFRARED INSPECTION FOR DETERMINING RESIDUAL FILMS ON SEMICONDUCTOR DEVICES

(75) Inventors: John L. Nistler, Martindale; Christopher H. Raeder, Austin, both of TX (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 0 days.

(21) Appl. No.: 09/536,659

(22) Filed: Mar. 28, 2000

(51) Int. Cl.$^7$ .................................. G01J 5/02

(52) U.S. Cl. .................... 250/341.4; 250/341.6; 374/129

(58) Field of Search .................. 250/340, 341.1, 250/341.4, 341.6, 339.11, 339.03; 374/121, 124, 129

(56) References Cited

U.S. PATENT DOCUMENTS

| 4,792,683 A | * 12/1988 | Chang et al. ............. 250/341.4 |
| 5,249,142 A | * 9/1993 | Shirakawa et al. ..... 250/339.03 |
| 5,294,198 A | 3/1994 | Schlagheck ................. 374/4 |
| 5,321,265 A | 6/1994 | Block ......................... 250/343 |
| 5,870,022 A | 2/1999 | Kuhnly et al. .............. 340/567 |
| 5,971,608 A | * 10/1999 | Koizumi ..................... 374/5 |

FOREIGN PATENT DOCUMENTS

| DE | 19526015 A1 | 7/1995 | ........... H01L/21/66 |
| EP | 59218938 | 10/1984 | .......... G01N/21/88 |
| EP | 03022531 | 1/1991 | ......... H01L/21/303 |
| EP | 07245284 | 9/1995 | ......... H01L/00/304 |
| WO | WO 98/32165 | 7/1998 | |

OTHER PUBLICATIONS

Stanley Wolf and Richard N. Tauber; *Silicon Processing for the VLSI Era, vol. 1: Process Technology;* pp. 446–452; 1986.

Hughes Electronics; Electro–Optical Sensor Materials and Processes–Sensors and Materials laboratory; pp. 1 & 4; Sep. 1999.

E. Neil Lewis, et al.; *Si: As Focal–Plane Array Detection for Fourier Transform Spectroscopic Imaging in the Infrared Fingerprint Region; Applied Spectroscopy;* vol. 51; No. 4; pp. 563–567; 1997.

F. Ferrieu; *Infrared spectroscopic ellipsometry using a Fourier transform infrared spectrometer: Some applications in thin–film characterization;* Review of Scientific Instruments, American Institute of Physics; vol. 60; No. 10; pp. 3212–3216; Oct. 1989.

L.H. Kidder et al.; *Mercury cadmium telluride focal–plane array detection for mid–infrared Fourier–transform spectroscopic imaging;* Optical Society of America; vol. 22; No. 10; pp. 742–744; 1997.

* cited by examiner

*Primary Examiner*—Huy Mai
(74) *Attorney, Agent, or Firm*—Timothy M. Honeycutt

(57) ABSTRACT

Various methods of inspecting a film on a semiconductor workpiece for a residue are provided. In one aspect, a method of inspecting a film on a semiconductor workpiece wherein the film has a known infrared signature is provided. The method includes heating the workpiece so that the film emits infrared radiation and sensing the infrared radiation emitted from the film. The infrared signature of the radiation emitted from the film is compared with the known infrared signature and a signal indicative of a deviation between the infrared signature of the emitted infrared radiation and the known infrared signature is generated. The method enables the rapid and accurate detection of residues, such as oxide residues on nitride films.

31 Claims, 2 Drawing Sheets

_US 6,452,180 B1_

INFRARED INSPECTION FOR DETERMINING RESIDUAL FILMS ON SEMICONDUCTOR DEVICES

BACKGROUND OF THE INVENTION

1. Field of the Invention

This invention relates generally to semiconductor processing, and more particularly to a method of inspecting a film on a semiconductor workpiece for residues.

2. Description of the Related Art

Inspection has been an integral component of semiconductor processing since the development of the earliest germanium-based bipolar integrated circuits. The need for inspection then and now stems from both engineering and economic considerations. Process engineers must be able to track the behavior of the multitude of individual process steps used to fabricate a given integrated circuit. From an economic standpoint, it is critical for semiconductor manufacturers to be able to quickly pinpoint the origin of unacceptable yields so that the circuit design or the fabrication process may be altered as necessary without needlessly wasting lots of wafers that may cost several hundred thousand dollars or more.

Morphology of VLSI and ULSI structures is generally determined by three microscopic techniques, namely, optical microscopy, scanning electron microscopy ("SEM"), and transmission electron microscopy ("TEM"). Optical microscopy is useful for studying wide field of use structures and structures that do not require magnification greater than about 1000x. SEM imaging involves the detection of secondary electrons emitted from a surface bombarded by a primary electron beam, and can yield information on line width, film thickness, step coverage, edge profiles after etch and other morphology data. SEM imaging has a maximum magnification value that is several orders of magnitude greater than the maximum magnification possible using optical microscopy. TEM imaging involves the production of an image due to the differential loss of electrons from an incident beam as it passes through a very thin film sample. The sample image must be thin enough to transmit the beam so that essential information caused by differences in sample thickness, phase composition and other irregularities is preserved. TEM imaging, while limited to particular film thicknesses, has a larger maximum magnification value than SEM imaging.

Various types of surface anomalies have proven difficult to detect using the aforementioned optical, SEM and TEM techniques. For example, residual oxide films an underlying nitride films have been historically difficult to see using optically microscopy. The problem stems from the behavior of light reflected from the oxide residue and the underlying nitride film. If the incident illuminating light is normal to the films, light reflected from the oxide film may not be differentiated from light reflected from the nitride film. If the incident light is protected at a low angle relative to the plane of the films, surface topography may prevent differentiation of light reflected by the oxide versus the nitride films. While SEM techniques are not prone to the light reflecting issues, structures with irregular topography, such as high aspect ratio trenches, may be not adequately imaged with SEM. As to TEM imaging techniques, relatively thick films may not be adequately imaged for residue detection purposes.

The problem of residue detection is not confined to residual oxide on nitride films. There are numerous situations in modern semiconductor processing where residual films may adversely impact device performance or yield. Residual resist on polysilicon structures and residual silicon oxynitride anti-reflective coating on metal layers represent just two such examples.

The present invention is directed to overcoming or reducing the effects of one or more of the foregoing disadvantages.

SUMMARY OF THE INVENTION

In accordance with one aspect of the present invention, a method of inspecting a film on a semiconductor workpiece wherein the film has a known infrared signature is provided. The method includes heating the workpiece so that the film emits infrared radiation and sensing the infrared radiation emitted from the film. The infrared signature of the radiation emitted from the film is compared with the known infrared signature and a signal indicative of a deviation between the infrared signature of the emitted infrared radiation and the known infrared signature is generated.

In accordance with another aspect of the present invention, a method of inspecting a film on a semiconductor workpiece wherein the film has a known infrared signature is provided. The method includes heating the workpiece so that the film emits infrared radiation and sensing the infrared radiation emitted from the film with an infrared camera that has a field of view defined by a plurality of pixels and is operable to sense an infrared signature corresponding to each pixel. The infrared signature of the radiation emitted from the film at each pixel is compared with the known infrared signature and a signal indicative of a deviation between the infrared signature of the emitted infrared radiation at each pixel and the known infrared signature is generated.

In accordance with another aspect of the present invention, a method of inspecting a silicon nitride film for the presence of residual oxide wherein the silicon nitride film has a known infrared signature is provided. The method includes heating the workpiece so that the silicon nitride film emits infrared radiation and sensing the infrared radiation emitted from the silicon nitride film. The infrared signature of the radiation emitted from the silicon nitride film is compared with the known infrared signature of the silicon nitride film and a signal indicative of a deviation between the infrared signature of the radiation emitted from the silicon nitride film and the known infrared signature is generated.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
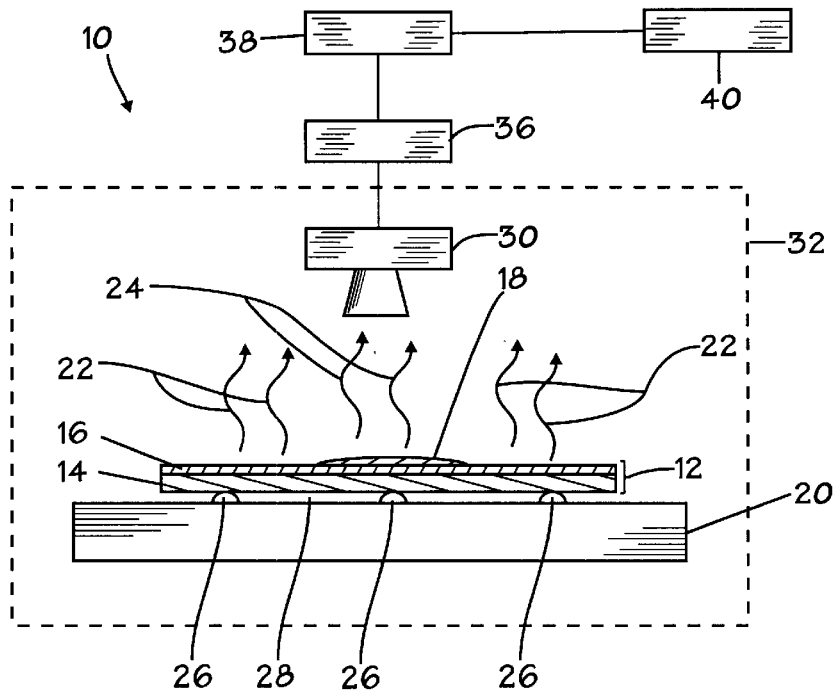
FIG. 1 is a schematic side view of an exemplary embodiment of an infrared inspection system in accordance with the present invention.

In the drawings described below, reference numerals are generally repeated where identical elements appear in more than one figure. Turning now to the drawings, and in particular to FIG. 1, therein is shown a schematic side view of an exemplary embodiment of an infrared inspection system 10 that is operable to sense and interpret infrared emissions from a semiconductor workpiece 12. In the illustrated embodiment, the workpiece 12 consists of a substrate 14, an overlying film 16 and a residue film 18. The workpiece 12 is seated on a heated stage 20. The stage 20 is brought to an elevated temperature to heat the workpiece 12 to stimulate the emission of infrared radiation 22 from the film 16 and infrared radiation 24 from the residual film 18.

When heated to the same temperature, different solids emit different infrared signatures. As described more fully below, this difference is infrared signatures is used in accordance with the present invention to differentiate unwanted residues from underlying films and thus provide for the rapid detection of residue films, such as the film 18.

The stage 20 is advantageously composed of a noncorroding material capable of withstanding elevated temperatures, such as, for example, stainless steel, boron nitride or the like. The stage 20 is heated by a boron nitride shrouded silicon carbide resistance heating element (not shown). To avoid the potential for thermal damage to the workpiece 12 during the heating process, the workpiece 12 is not actually laid upon the upper surface of the stage 20. Rather, a plurality of bumps or beads 26 are disposed between the stage 20 and the workpiece 12 and the heating of the workpiece 12 is accomplished by way of convective heat transfer in the gap 28 between the workpiece 12 and the stage 20. The bumps 26 may be composed of a variety of materials exhibiting low chemical reactivity and wear resistance such as, for example, garnet, topaz, ruby or the like.

The infrared emissions 22 and 24 from the films 16 and 18 are sensed by an infrared sensor 30. In an exemplary embodiment, the sensor 30 is an infrared camera. The camera 30 is movable vertically with respect to the workpiece 12 and in a plane approximately parallel to the plane of the workpiece 12. The vertical and horizontal movements of the camera 30 are provided by conventional drive mechanisms (not shown). To eliminate the capture of unwanted infrared noise signals, the stage 20, the workpiece 12, and the infrared camera 30 are positioned within a thermally stable enclosure 32.

Figure 2:
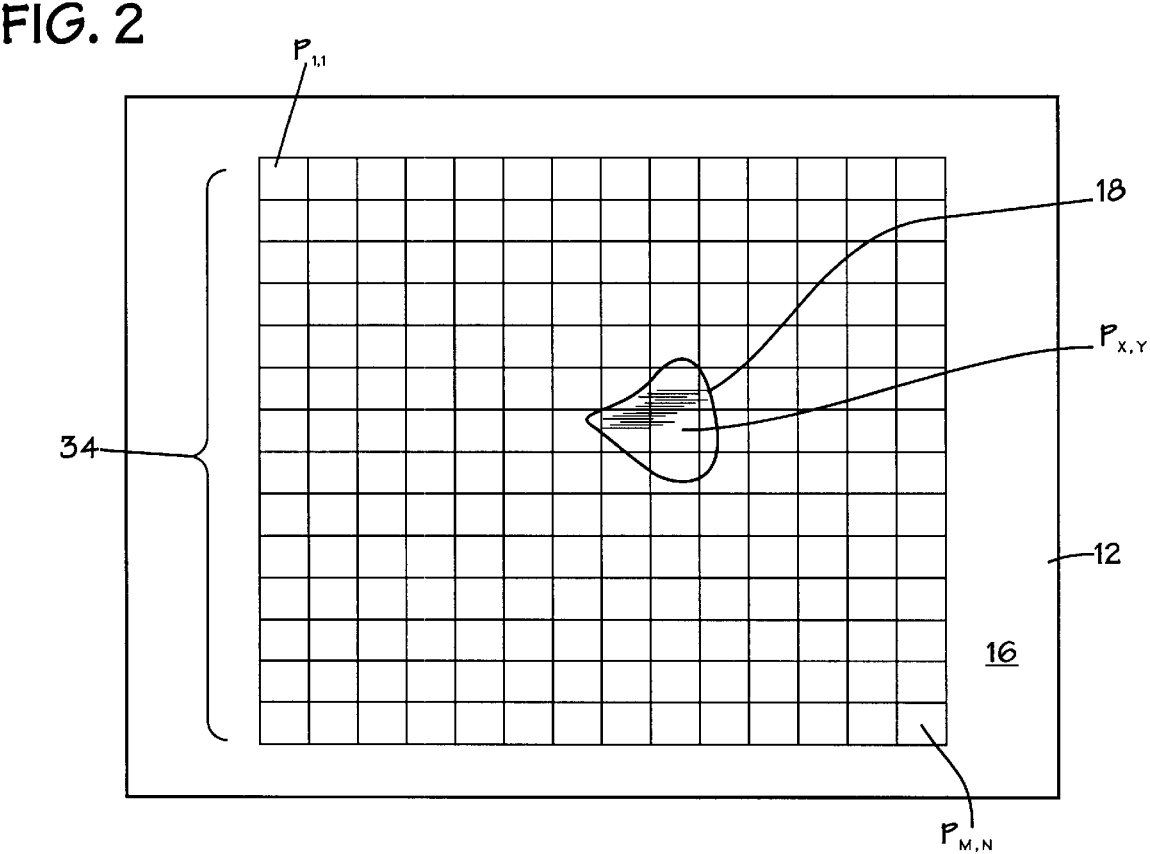
FIG. 2 is a plan view of two films on a semiconductor workpiece undergoing inspection in accordance with the present invention.

The infrared data acquisition by the infrared camera 30 may be understood by referring now to FIG. 2, which is a plan view of the film 16 and the residue film 18. The infrared camera 30 has a field of view 34 that is defined by a plurality of pixels, $P_{1,1}$ to $P_{M,N}$. A subset of the plurality of pixels $P_{1,1}$ to $P_{M,N}$ corresponds to the location of the residue film 18. One of the pixels that corresponds to the location of the residue film 18 is designated $P_{X,Y}$. The camera 30 may consist of a single infrared sensor that is scanned across the surface of the film 16 according to the pixel pattern 34, or may be configured with a plurality of detector cells, each dedicated to a particular pixel, e.g, $P_{1,1}$ etc. In an exemplary embodiment, the camera 30 is provided with a plurality of individual detector cells dedicated to individual pixels. The camera 30 senses the infrared emission at each pixel and generates a signal based upon the sensed infrared radiation. The radiation emitted at each pixel is converted into a signal that is passed to a multiplexing scanner 36 that is addressed in a well-known fashion by an electronic controller 38. The electronic controller 38 is provided with an analog-to-digital converter. The scanning multiplexer 36 supplies a sequence of signals to the analog-to-digital converter of the controller 38. The sequence of signals is representative of the infrared radiation emitted at the pixels $P_{1,1}$ to $P_{M,N}$. The signals supplied to the analog-to-digital converter in the electronic controller 38 are then routed to a memory unit 40 for storage. The memory unit 40 additionally stores data corresponding to the known infrared signature for the film 16. The electronic controller 38 generates signals indicative of the infrared signature at each of the pixels $P_{1,1}$ to $P_{M,N}$ and compares those signals to signals corresponding to the known infrared signature for the film 16. If any pixel has an infrared signature that deviates from the known infrared signature for the film 16, the electronic controller 38 generates a signal indicating the presence of a residue film on the film 16, in this case the residue film 18.

Figure 3:
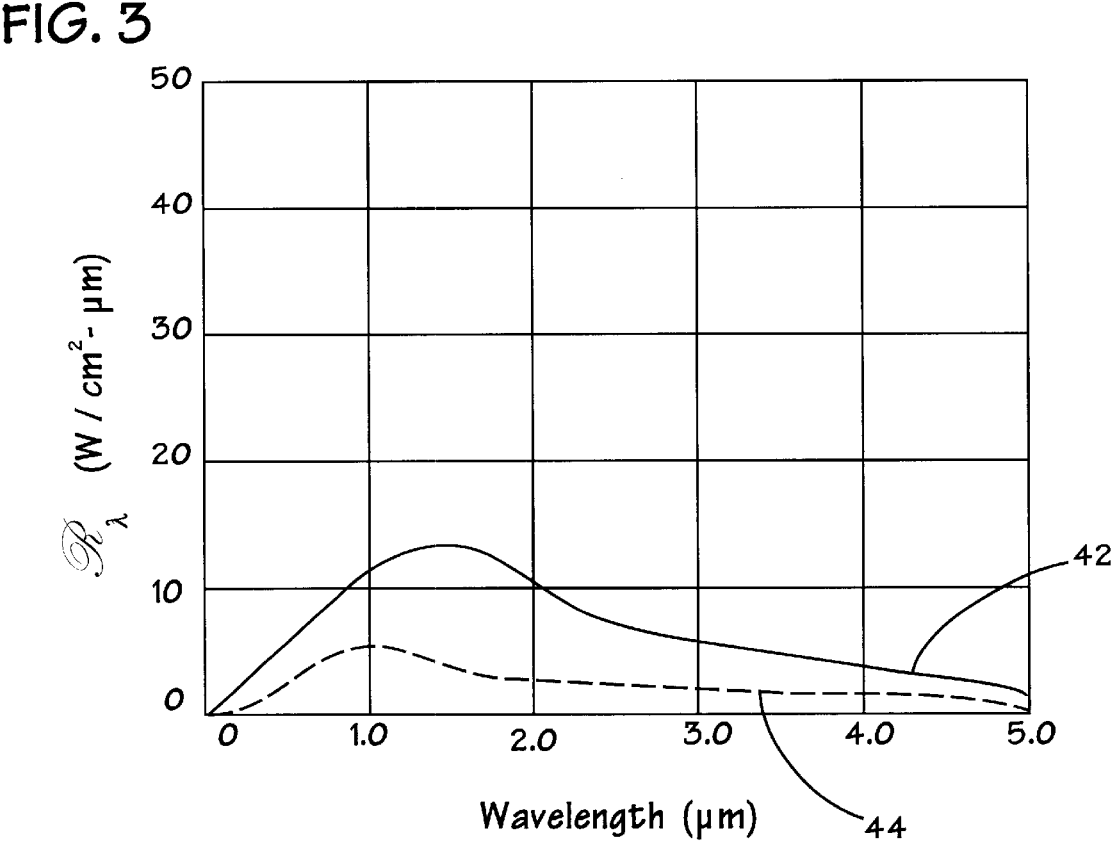
FIG. 3 is a plot of the known spectral radiancy for one of the two films of FIG. 2 and the spectral radiancy emanating from a pixel on the other of the two films of FIG. 2 versus wavelength for a hypothetical wavelength interval in accordance with the present invention.

Depending upon the capabilities of the infrared camera 30, infrared signatures of various characters may be sampled and compared to inspect for die presence of the residue film 18. For example, if the camera 30 is able to sample infrared radiation over a wavelength interval, the spectral radiancy $\mathcal{R}_{measured}$ over a wavelength interval in the infrared portion of the electromagnetic spectrum may be detected for each pixel a $P_{1,1}$ to $P_{M,N}$ and compared with the known spectral radiancy $\mathcal{R}_{known}$ for the film 16 as illustrated in FIG. 3. In general, the spectral radiancy $\mathcal{R}$ is defined so that the quantity $\mathcal{R}d\lambda$ is the rate at which energy is radiated per unit area of surface for wavelengths lying in the interval $\lambda$ to $\lambda+d\lambda$. FIG. 3 depicts a plot 42 of the known spectral radiancy $\mathcal{R}_{known}$ for the film 16 and a plot 44 of the spectral radiancy $\mathcal{R}_{measured}$ emanating from the pixel $P_{X,Y}$ versus wavelength for a hypothetical wavelength interval of 0,0 to 5.0 $\mu$m and a temperature T of the workpiece 12. For very material there exists a family of spectral radiancy curves like those shown in FIG. 3, one curve for every temperature. Accordingly, the plots 42 and 44 correspond to a particular temperature T of the workpiece 12 (see FIG. 1). The plot 44 deviates significantly from the plot 42 of the known spectral radiancy $\mathcal{R}_{known}$ for the film 16, and thus indicates the presence of a residue film 18 on the film 16. A comparison of the plots 42 and 44 reveals a significant deviation between the spectral radiancy $\mathcal{R}_{measured}$ at the pixel $P_{X,Y}$ and the known spectral radiancy $\mathcal{R}_{known}$ for the film 16. This deviation is thus indicative of the presence of a residue film 18 on the film 16.

The data comparisons are made by the controller 38. The data underlying the plot 44 is sensed and stored to memory 40. The data underlying the plot 42 is stored in the memory unit 40 in advance of the inspection and recalled when necessary by the electronic controller 38 and compared with the spectral radiancy data underlying the plot 44.

If desired, less than the entirety of the plots 42 and 44 may be sampled and used as a basis for comparison. For example, the spectral radiancy for the interval 1.0 to 2.0 $\mu$m may be used as a basis for comparison. Similarly, the radiancy for every pixel may be sampled at a single wavelength, for example, 1.0 $\mu$m, and compared with the known radiancy of the film 16 at that wavelength and temperature. Alternatively, the radiancy $\mathcal{R}$ over the entire spectrum interval for the plots 42 and 44 may be computed according to the following equation:

$$\mathcal{R} = \int_0^5 \mathcal{R}\lambda d\lambda$$

and used as a basis for comparison.

Note that it is desirable to cancel out minor temperature variations in the film 16 that do not suggest the presence of a residue film. Such low level temperature deviations may be the result of topographical irregularities in the film 16 or in structures underlying the film 16. Accordingly, the gain associated with the comparison of the infrared signature for a given pixel and the known infrared signature for the film 16 should be reduced so that low level variations in temperature will not trigger the generation of a defect alarm.

In operation, the workpiece 12 is placed inside the chamber 32 and seated on the supporting bumps 26. The stage 20 may be preheated to the desired temperature at this point or may be brought to temperature. It is desirable for the stage 20 to be heated to a temperature that produces a temperature T of about 50 to 250° C. in the workpiece 12. The low end of the temperature range ensures that the workpiece 12 will be heated sufficiently above room temperature so that signal noise associated with the radiation emitted from the walls of the chamber 32 and other structures will not interfere with the processing of the infrared signatures from the film 16 to the film 18. A higher temperature than 250° C. may be used so long as thermal budgeting concerns for the workpiece 12 are taken into account. It is anticipated that the workpiece 12 will come to a stable temperature T in about ten seconds or less. When the temperature of the workpiece 12 has stabilized, the camera 30 is activated and the film 16 is scanned according to the pixel pattern depicted in FIG. 2. In response, the electronic controller 38 generates a series of signals indicative of the infrared signature for each of the pixels $P_{1,1}$ to $P_{M,N}$ and compares the infrared signature for each pixel with the known infrared signature for the film 16. For each pixel where there is a deviation in the infrared signatures between the pixel and the known infrared signature for the film 16, the controller 38 generates a signal indicating that deviation. The signals indicative of the deviations in infrared signatures generated by the controller 38 may be in the form of code for use with another controller device (not shown) and/or may be output in the form of a human readable color display on a monitor (not shown) wherein pixels that have deviant infrared signatures are displayed with a different shade than those conforming to the infrared signatures known for the film 16.

If desired, the heating and data acquisition may be cycled to obtain a larger sample for a given workpiece. For example, the workpiece 12 may be heated and the infrared signature of the emitted infrared radiation may be sensed and compared with known signatures. The workpiece 12 may then be cooled, either by refrigeration or natural heat loss, and then reheated to obtain another set of infrared signature data. This may be repeated as often as desired so long as thermal budgeting concerns are considered.

If the workpiece 12 is patterned with a plurality of die, infrared scanning of the film 16 may be made on a die-to-die basis. For example, the film 16 on one of the die may be imaged and that infrared signature data used as a known signature for a comparison with the signature from the film 16 on a second die. Inspection times may be enhanced as die-to-die comparison can often be performed more quickly than die-to-database comparisons.

Figure 4:
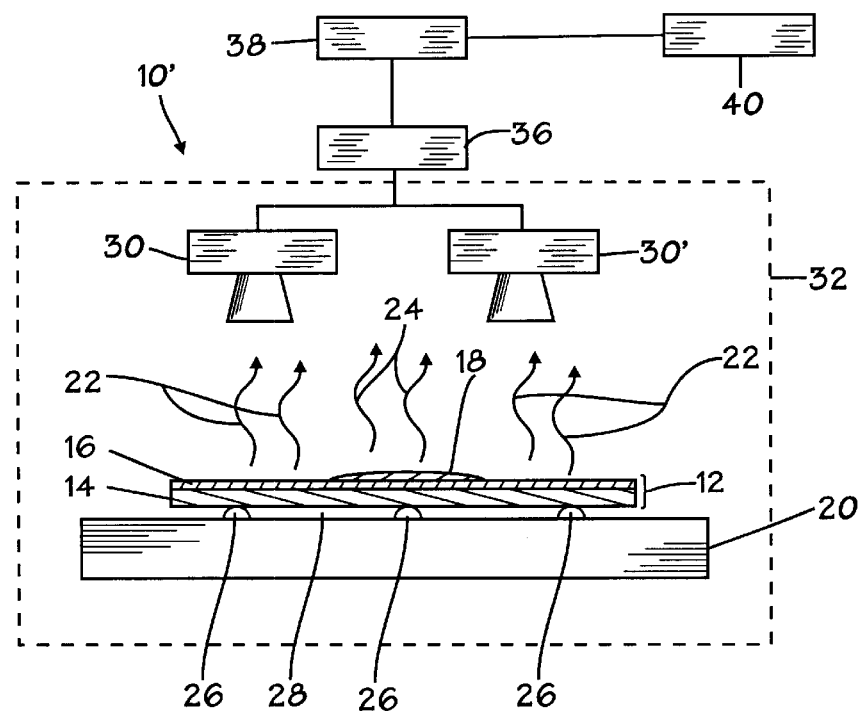
FIG. 4 is a schematic side view of an alternate exemplary embodiment of an infrared inspection system in accordance with the present invention.

FIG. 4 depicts schematic side view of an alternate exemplary infrared inspection system 10' that utilizes multiple sensors to sense and interpret infrared emissions from the semiconductor workpiece 12. The system 10' includes the same basic components and utilizes the same data acquisition and processing methodology of the embodiment of the system 10 described above and shown in FIG. 1. However, a second infrared sensor 30' is used in concert with the sensor 30. Various scanning techniques may be employed with this arrangement. For example, two portions of the workpiece 12 may be separately imaged and compared. This technique may be useful if the workpiece 12 is patterned with a plurality of die, and infrared scanning of the film 16 on a die-to-die basis is desired. As with the aforementioned embodiment, the film 16 on one of the die may be imaged and that infrared signature data used as a known signature for a comparison with the signature from the film 16 on a second die and other scanned die. In another option, the same portion of the workpiece 12 may be scanned with both sensors 30 and 30' and those infrared signatures compared to verify the accuracy of the first scan. If desired, more than two sensors may be employed.

The skilled artisan will appreciate that the methods of the present invention provide for rapid and accurate differentiation of residues present on underlying films. Examples of potential uses are legion and include such circumstances as the detection of residual oxide on nitride films, residual resist on polysilicon structures and residual anti-reflective coatings over metal layers to name just a few. The method is well suited for automated defect inspection techniques.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of inspecting a film on a semiconductor workpiece, the film having a known infrared signature indicative of the composition of the film, comprising:

heating the workpiece so that the film emits infrared radiation;

sensing the infrared radiation emitted from the film;

comparing the infrared signature of the radiation emitted from the film with the known infrared signature; and generating a signal indicative of a deviation between the infrared signature of the emitted infrared radiation and the known infrared signature, the deviation being indicative of the presence of another material on the film.

2. The method of claim 1, wherein the known infrared signature comprises the spectral radiancy of the film over a given wavelength interval and the infrared signature of the radiation emitted from the film comprises the spectral radiancy of the emitted radiation over the given wavelength interval.

3. The method of claim 1, wherein the known infrared signature comprises the radiancy of the film over a given wavelength interval and the infrared signature of the radiation emitted from the film comprises the radiancy of the emitted radiation over the given wavelength interval.

4. The method of claim 1, wherein the known infrared signature comprises the radiancy of the film at a given wavelength and the infrared signature of the radiation emitted from the film comprises the radiancy of the emitted radiation at the given wavelength.

5. The method of claim 1, wherein the emitted radiation is sensed with an infrared sensor having a field of view defined by a plurality of pixels and being operable to sense an infrared signature corresponding to each pixel, the comparison of the infrared signature of the radiation emitted from the film with the known infrared signature being performed for each pixel.

6. The method of claim 1, wherein the emitted radiation is sensed with an infrared camera.

7. The method of claim 1, wherein the emitted radiation is sensed with a plurality of infrared cameras.

8. The method of claim 1, wherein the comparison of the infrared signature of the radiation emitted from the film with the known infrared signature and the generation of a signal indicative of a deviation between the infrared signature of the emitted infrared radiation and the known infrared signature is performed with an electronic controller.

9. The method of claim 8, wherein the electronic controller comprises a computer.

10. The method of claim 1, wherein the film comprises silicon nitride.

11. The method of claim 1, wherein the process of heating the workpiece and acquiring an infrared signature is performed, the workpiece is cooled, and process of heating the workpiece and acquiring an infrared signature is repeated.

12. The method of claim 1, wherein the film is positioned on a first die and a second die of the workpiece and the infrared signature of the radiation emitted from the film on the first die is compared with the infrared signature of the radiation emitted from the second die, the infrared signature of the radiation emitted from the film on the first die film comprising the known infrared signature.

13. A method of inspecting a silicon nitride film on a workplace for the presence of residual oxide, the silicon nitride film having a known infrared signature, comprising:

heating the workpiece so that the silicon nitride film emits infrared radiation;

sensing the infrared radiation emitted from the silicon nitride film;

comparing the infrared signature of the radiation emitted from the silicon nitride film with the known infrared signature of the silicon nitride film; and generating a signal indicative of a deviation between the infrared signature of the radiation emitted from the silicon nitride film and the known infrared signature.

14. The method of claim 13, wherein the known infrared signature comprises the radiancy of the film over a given wavelength interval and the infrared signature of the radiation emitted from the film comprises the radiancy of the emitted radiation over the given wavelength interval.

15. The method of claim 13, wherein the known infrared signature comprises the radiancy of the film at a given wavelength and the infrared signature of the radiation emitted from the film comprises the radiancy of the emitted radiation at the given wavelength.

16. The method of claim 13, wherein the known infrared signature comprises the spectral radiancy of the film over a given wavelength interval and the infrared signature of the radiation emitted from the film comprises the spectral radiancy of the emitted radiation over the given wavelength interval.

17. The method of claim 13, wherein the emitted radiation is sensed with an infrared sensor having a field of view defined by a plurality of pixels and being operable to sense an infrared signature corresponding to each pixel, the comparison of the infrared signature of the radiation emitted from the film with the known infrared signature being performed for each pixel.

18. The method of claim 13, wherein the comparison of the infrared signature of the radiation emitted from the film at each pixel with the known infrared signature and the generation of a signal indicative of a deviation between the infrared signature of the emitted infrared radiation at each pixel and the known infrared signature is performed with an electronic controller.

19. The method of claim 13, wherein the emitted radiation is sensed with a plurality of infrared cameras.

20. The method of claim 13, wherein the silicon nitride film is positioned on a first die and a second die of the workpiece and the infrared signature of the radiation emitted from the film on the first die is compared with the infrared signature of the radiation emitted from the second die, the infrared signature of the radiation emitted from the film on the first die film comprising the known infrared signature.

21. A method of inspecting a film on a first die and a second die of a semiconductor workpiece, the film having a known infrared signature, comprising:

heating the workpiece so that the film emits infrared radiation;

sensing the infrared radiation emitted from the film;

comparing the infrared signature of the radiation emitted from the film on the first die with the infrared signature of the radiation emitted from the second die, the infrared radiation emitted from the film on the first die being the known infrared signature; and generating a signal indicative of a deviation between the infrared signature of the emitted infrared radiation and the known infrared signature.

22. The method of claim 21, wherein the known infrared signature comprise the spectral radiancy of the film over a given wavelength interval and the infrared signature of the radiation emitted from the film comprises the spectral radiancy of the emitted radiation over the given wavelength interval.

23. The method of claim 21, wherein the known infrared signature comprises the radiancy of the film over a given wavelength interval and the infrared signature of the radiation emitted from the film comprises the radiancy of the emitted radiation over the given wavelength interval.

24. The method of claim 21, wherein the known infrared signature comprises the radiancy of the film at a given wavelength and the infrared signature of the radiation emitted from the film comprises the radiancy of the emitted radiation at the given wavelength.

25. The method of claim 21, wherein the emitted radiation is sensed with an infrared sensor having a field of view defined by a plurality of pixels and being operable to sense an infrared signature corresponding to each pixel, the comparison of the infrared signature of the radiation emitted from the film with the known infrared signature being performed for each pixel.

26. The method of claim 21, wherein the emitted radiation is sensed with an infrared camera.

27. The method of claim 21, wherein the emitted radiation is sensed with a plurality of infrared cameras.

28. The method of claim 21, wherein the comparison of the infrared signature of the radiation emitted from the film with the known infrared signature and the generation of a signal indicative of a deviation between the infrared signature of the emitted infrared radiation and the known infrared signature is performed with an electronic controller.

29. The method of claim 28, wherein the electronic controller comprises a computer.

30. The method of claim 21, wherein the film comprises silicon nitride.

31. The method of claim 21, wherein the process of heating the workpiece and acquiring an infrared signature is performed, the workpiece is cooled, and process of heating the workpiece and acquiring an infrared signature is repeated.

* * * * *

UNITED STATES PATENT AND TRADEMARK OFFICE
CERTIFICATE OF CORRECTION

| | | |
|---|---|---|
| PATENT NO. | : 6,452,180 B1 | Page 1 of 1 |
| APPLICATION NO. | : 09/536659 | |
| DATED | : September 17, 2002 | |
| INVENTOR(S) | : John L. Nistler et al. | |

It is certified that error appears in the above-identified patent and that said Letters Patent is hereby corrected as shown below:

In claim 13, line 24, delete the word "workplace" and substitute the word --workpiece-- therefor; and In claim 31, line 63, insert the word --the-- between the words "and" and "process".

Signed and Sealed this

Fifth Day of December, 2006

JON W. DUDAS
*Director of the United States Patent and Trademark Office*